United States Patent
Kerlin et al.

(10) Patent No.: US 12,216,130 B2
(45) Date of Patent: Feb. 4, 2025

(54) FACTOR XIII IMMUNOASSAY

(71) Applicant: The Research Institute at Nationwide Children's Hospital, Columbus, OH (US)

(72) Inventors: Bryce A Kerlin, Galena, OH (US); Michael A. Durda, Columbus, OH (US); Amanda P. Waller, Whitehall, OH (US); Katelyn J. Wolfgang, Hilliard, OH (US)

(73) Assignee: The Research Institute at Nationwide Children's Hospital, Columbus, OH (US)

(*) Notice: Subject to any disclaimer, the term of this patent is extended or adjusted under 35 U.S.C. 154(b) by 951 days.

(21) Appl. No.: 17/290,369

(22) PCT Filed: Oct. 30, 2019

(86) PCT No.: PCT/US2019/058820
§ 371 (c)(1),
(2) Date: Apr. 30, 2021

(87) PCT Pub. No.: WO2020/092531
PCT Pub. Date: May 7, 2020

(65) Prior Publication Data
US 2021/0405073 A1    Dec. 30, 2021

Related U.S. Application Data

(60) Provisional application No. 62/752,532, filed on Oct. 30, 2018.

(51) Int. Cl.
*G01N 33/53*   (2006.01)
*G01N 33/543*   (2006.01)
*G01N 33/86*   (2006.01)

(52) U.S. Cl.
CPC .......... *G01N 33/86* (2013.01); *G01N 33/543* (2013.01); *G01N 2333/91085* (2013.01)

(58) Field of Classification Search
None
See application file for complete search history.

(56) References Cited

U.S. PATENT DOCUMENTS 5,508,202 A * 4/1996 Enomoto .................. C12Q 1/56
422/534

FOREIGN PATENT DOCUMENTS

WO    WO9117444    * 5/1991    .......... G01N 33/573
WO    WO2005038045    * 4/2005    .............. C12Q 1/28

* cited by examiner

*Primary Examiner* — Gary Counts
(74) *Attorney, Agent, or Firm* — Tarolli, Sundheim, Covell & Tummino LLP

(57) ABSTRACT

A method of detecting factor XIII activity in a biological sample is described. The method includes the steps of immobilizing or having obtained a capture antibody on a solid support, wherein the capture antibody comprises an antibody or antibody fragment that specifically binds to fibrinogen; incubating the biological sample with the capture antibody; contacting the immobilized capture antibody with α-thrombin, calcium, and α2-antiplasmin (AP); contacting the immobilized capture antibody with a detection antibody or antibody fragment that specifically binds to α2-AP, wherein the detection antibody or antibody fragment includes a detection label; and determining that factor XIII activity is present if the detection label is detected. The method can be used to diagnose a subject having factor XIII deficiency, or to monitor factor XIII levels in a subject undergoing factor XIII replacement therapy.

17 Claims, 6 Drawing Sheets

FACTOR XIII IMMUNOASSAY

CROSS-REFERENCE TO RELATED APPLICATIONS

This application was a national stage application claiming the benefit of International Patent Application No. PCT/US2019/058820, filed on Oct. 30, 2019, which claimed the benefit of U.S. Provisional Application No. 62/725,532, filed Oct. 30, 2018, both of which are incorporated herein by reference.

BACKGROUND

Congenital factor XIII (fXIII) deficiency is a rare, severe bleeding disorder affecting an estimated 1 in 2 million persons, but is more prevalent in cultures with a high rate of consanguinity. In 2015 the World Federation of Hemophilia annual global survey identified 1,485 persons with fXIII deficiency. However, while 111 (57%) of 195 nations responded to the survey, covering an estimated 91% of the global population, only 66 (34%) of the nations reported specifically on fXIII deficiency prevalence. This suggests that fXIII deficiency is under-recognized, resulting in under-reported prevalence. Thus, on a global scale, many patients are predicted to be undiagnosed (e.g. based on current global census estimates (7.5 billion), there should be an estimated 3,750 patients with severe deficiency). The prevalence of heterozygous fXIII deficiency (i.e. carriers) remains poorly defined, but has been estimated to be 1 in 1,000 (e.g. 7.5 million persons worldwide). Moreover, heterozygous and other mild fXIII deficiencies have been reported to be associated with clinically significant bleeding symptoms, especially following hemostatic challenges (e.g. trauma, surgery, peripartum, etc.).

Recent advancements in both plasma-derived and recombinant fXIII pharmaceuticals have dramatically improved clinical outcomes for patients with severe deficiency. Kerlin et al. J Thromb Haemost, 12: 2038-43 (2014). Consequently, there is a movement in the field to determine how these therapies may benefit those with moderate or mild deficiency. Menegatti et al., J Thromb Haemost., 15(9):1728-1736 (2017). However, both the accurate diagnosis of disease severity and pharmacokinetic monitoring of fXIII supplementation therapy is currently hampered by the lack of a convenient, easily implemented, and highly sensitive fXIII activity assay with the ability to reliably measure activities<10% (0.1 IU/mL). Lawrie et al., J Thromb Haemost, 8: 2478-82 (2010).

The currently available, clinically-approved assays are technically challenging to implement due to the complex blanking procedures necessary to obtain measurements in the lower end of the dynamic range. Ajzner E, Muszbek L., J Thromb Haemost, 2: 2075-7 (2004). Therefore, the assays are often available only in large reference laboratories hindering their utility for directly monitoring therapy during critical clinical scenarios (i.e. surgery, trauma, pregnancy, etc.). The inconvenience of reference laboratory testing likely contributes to an over-reliance on screening assays (e.g. 5M urea clot lysis) that are known to have limited sensitivity and specificity. Kohler et al., J Thromb Haemost, 9: 1404-6 (2011). Because these screening assays only detect severe deficiency, this may contribute to the under-recognition of moderate and mild deficiency. Thus, there is a critical need to develop new, simplified fXIII activity assays able to reliably and accurately measure activities across the dynamic range, including in the lower end of the range (<10%) in an easily implemented assay platform. It is our expectation that successful development and eventual commercialization of the proposed assay will improve the accurate and timely diagnosis of fXIII deficiency, across the phenotypic spectrum (i.e. mild, moderate, severe), and enable appropriate therapeutic monitoring.

The currently available, clinically-approved fXIII activity assays are based upon an indirect measurement of activated fXIII (fXIIIa) enzymatic activity. FXIII is a transglutaminase that drives the formation of a peptide bond between an acyl group and a free amine group (on a neighboring peptide). During an intermediate step of the reaction, a thioacyl complex is formed between the acyl donor peptide and the active site cysteine of fXIIIa and an ammonia ($NH_3$) molecule is released. Thus, the currently available, clinically-approved assays rely on the measurement of "$NH_3$-release" (i.e. increasing levels of free $NH_3$ in the reaction solution) via an NAD(P)H-dependent glutamate dehydrogenase reaction, with the reduction of NAD(P)H absorbance measured spectrophotometrically at 340 nm. Unfortunately, the assays are highly sensitive to fXIII-independent NAD(P)H-consuming and ammonia-producing reactions that may take place, physiologically, in the plasma sample (e.g. lactate dehydrogenase NADH consumption, γ-glutamyl transferase-dependent glutamine de-amidation). Due to these reactions the assays are prone to overestimate FXIIIa activity. Thus, careful blanking procedures are recommended to 'subtract' these non-specific NAD(P)H reducing plasma activities from the apparent fXIIIa measured activity, with variable success that is not reproducible in all labs.

More recently, a highly-sensitive assay that measures the isopeptidase activity of fXIIIa has been developed for research use only. Oertel et al. Analytical biochemistry, 367: 152-8 (2007). This fluorometric assay relies on the loss of a fluorescent quencher in a manner dependent upon the fXIIIa isopeptidase activity. The lower limit of detection was 2% (0.02 IU/mL), with a quantitation limit of 5% (0.05 IU/mL). Importantly, the NADH-reduction method overestimated fXIIIa activity in comparison to the isopeptidase method. Thus, while this method offers a promising improvement, the isopeptidase activity is likely less (patho)physiologically relevant than the transglutaminase activity (which crosslinks α2-AP to fibrinogen), which is not captured directly by this method. Fraser et al., Blood, 117: 6371-4 (2011). A number of amine incorporation assays have been developed to directly measure the transglutaminase activity of fXIIIa. These assays rely on accurate measurement of remaining, unincorporated amines after a step to separate them from the substrate. These assays are highly sensitive, but are not commonly employed in the clinical setting due to their time-consuming nature and poor standardization properties.

SUMMARY OF THE INVENTION

Factor XIII deficiency is a rare and potentially under recognized severe bleeding disorder. Appropriate diagnosis is hampered, in part, by a lack of highly sensitive, easily implemented factor XIII activity assays. Thus, there is a critical need to discover and develop simplified, high sensitivity factor XIII activity assays. The inventors constructed a hybrid enzyme capture/enzyme-linked immunosorbent assay (EC-ELISA) to measure the transglutaminase activity of factor XIII. Recent discoveries suggest that factor XIII circulates in complex with fibrinogen and that a biologically important activity of factor XIII is to crosslink alpha-2-antiplasmin (α2-AP), a potent fibrinolysis inhibitor, to fibrin. The inventors capitalized on these discoveries to capture factor XIII with fibrinogen antibodies in an enzyme capture step and assess its activity via incorporation of α2-AP, using an ELISA step. The EC-ELISA will enable the direct measurement of activated factor XIII (fXIIIa) transglutaminase activity and will have high sensitivity at the low end of the dynamic range (<10%; <0.01 IU/mL).

The ISTH-SSC recommends that "A quantitative functional FXIII activity assay that detects all forms of FXIII deficiency should be used as a 'first-line' screening test". The EC-ELISA invention can perform in such a manner, with exceedingly rare exceptions, in a platform that can easily be implemented in both the research and clinical laboratory. This invention provides an improved diagnostic and monitoring assay that can improve care for patients afflicted with this rare, but potentially life-threatening disorder.

BRIEF DESCRIPTION OF THE FIGURES

The present invention may be more readily understood by reference to the following figures, wherein.

DETAILED DESCRIPTION OF THE INVENTION

Figure 1:
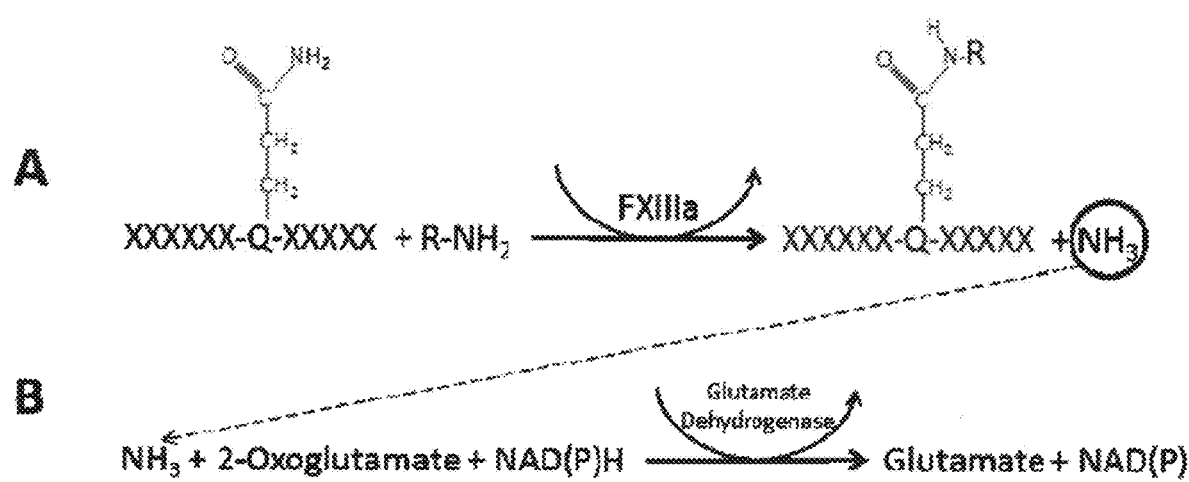
FIG. 1 provides a scheme showing that ammonia-release assays are based upon the transglutaminase reaction catalyzed by activated Factor XIII. (A) FXIIIa catalyzes the formation of an isopeptide bond. A free ammonia molecule is generated with the formation of each bond. (B) Ammonia levels serve as an indirect measure of transglutaminase activity in an ammonia-consuming side reaction producing NAD(P). Conversion of NAD(P)H to NAD(P) in this reaction is detected with a spectrophotometer by absorbance at the appropriate wavelength (340 nm). (Q: glutamine with its sidechain; X: any other amino acid; R: peptide; FXIIIa: activated plasma Factor XIII; $NH_3$: ammonia; NAD(P): nicotinamide adenine dinucleotide (phosphate))

Unless otherwise defined, all technical and scientific terms used herein have the same meaning as commonly understood by one of ordinary skill in the art to which these exemplary embodiments belong. The terminology used in the description herein is for describing particular exemplary embodiments only and is not intended to be limiting of the exemplary embodiments. As used in the specification and the appended claims, the singular forms "a." "an," and "the" are intended to include the plural forms as well, unless the context clearly indicates otherwise. All publications, patent applications, patents, and other references mentioned herein are incorporated by reference in their entirety.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

"Treating", as used herein, means ameliorating the effects of, or delaying, halting or reversing the progress of a disease or disorder. Treatment includes prophylactic treatment of subjects diagnosed with factor XIII deficiency who have not yet exhibited symptoms of the disease, and non-prophylactic treatment of subjects who have exhibited symptoms. The word encompasses reducing the severity of a symptom of a disease or disorder and/or the frequency of a symptom of a disease or disorder. A subject is successfully "treated" for a disease or disorder if the subject shows observable and/or measurable reduction in or absence of one or more signs and symptoms of a particular disease or condition.

As used herein, the term "diagnosis" can encompass determining the nature of disease in a subject, as well as determining the severity and probable outcome of disease or episode of disease and/or prospect of recovery (prognosis). "Diagnosis" can also encompass diagnosis in the context of rational therapy, in which the diagnosis guides therapy, including initial selection of therapy, modification of therapy (e.g., adjustment of dose and/or dosage regimen), and the like.

A "subject", as used therein, can be a human or non-human animal. Non-human animals include, for example, livestock and pets, such as ovine, bovine, porcine, canine, feline and murine mammals, as well as reptiles, birds and fish. Preferably, the subject is human. Subjects can also be selected from different age groups. For example, the subject can be a child, adult, or elderly subject.

The term antigen, as used herein, refers to a molecule or a portion of a molecule capable of being bound by an antibody which is additionally capable of inducing an animal to produce an antibody capable of binding to an epitope of that antigen. An antigen can have one or more than one epitope. The specific reaction referred to above is meant to indicate that the antigen will react, in a highly selective manner, with its corresponding antibody and not with the multitude of other antibodies which can be evoked by other antigens.

The term epitope, as used herein, refers to that portion of any molecule capable of being recognized by, and bound by, an antibody. In general, epitopes consist of chemically active surface groupings of molecules, for example, amino acids or sugar side chains, and have specific three-dimensional structural characteristics as well as specific charge characteristics. The epitopes of interest for the present invention are epitopes comprising amino acids.

As used herein, the term "immunoassay" refers to an assay in which an antibody (e.g. anti-α2-AP) specifically binds to a protein including an antigen recognized by the capture antibody (e.g. anti-fibrinogen) to provide for the detection and/or quantitation of the protein. An "immunoassay" can use a particular antibody to detect, isolate, target, and/or quantify the antibody that specifically binds to the capture antibody. One example of an "immunoassay" includes a capture antibody that contains one or more antigens to detect, isolate, and/or quantify one or more proteins in a sample.

Factor XIII Immunoassay

In one aspect, the present invention provides a method of detecting factor XIII activity in a biological sample. The method includes the steps of: a) immobilizing or having obtained a capture antibody on a solid support, wherein the capture antibody comprises an antibody or antibody fragment that specifically binds to fibrinogen; b) incubating the biological sample with the capture antibody; c) washing the immobilized capture antibody to remove unbound protein; d) contacting the immobilized capture antibody with α-thrombin, calcium, and α2-antiplasmin (AP); e) washing the immobilized capture antibody to remove unreacted α2-AP; f) contacting the immobilized capture antibody with a detection antibody or antibody fragment that specifically binds to α2-AP, wherein the detection antibody or antibody fragment includes a detection label; g) washing the immobilized capture antibody to remove unbound protein; and h) determining that factor XIII activity is present if the detection label is detected. Essentially, the method captures factor XIII with an anti-fibrinogen antibody, activates the factor XIII in the presence of α2-AP, and then detects factor XIII activity with an antibody that binds to α2-AP.

Congenitally fXIII deficient human plasma (George King Bio-Medical, Inc.) can be spiked with Tretten to known concentrations, beginning below the LLD, up to 100% (1.0 IU/mL). It is known that Tretten (recombinant factor XIII A-subunit protein), complexes with circulating free factor XIII B-subunit protein. Inbal et al., Blood, 119(22):5111-7 (2012) It is also known that the George King congenitally fXIII deficient plasma is derived from an A-subunit deficient donor. Nonetheless, was confirmed using western blots of the deficient plasma with A- and B-subunit antibodies. Based on the recent discovery that circulating fXIII is bound to fibrinogen via an interaction between the fXIII B-subunit and fibrinogen residues 1390-396, it is thought that 'free' factor XIII B-subunit actually circulates in complex with fibrinogen. Byrnes et al., Blood, 128(15):1969-78 (2016) Thus, the subsequent formation of the A2B2 complex would position A-subunits in a ternary complex with fibrinogen, essentially in juxtaposition to the site of physiologic necessity for hemostasis. Alternatively, the A2B2 heterotetramer may form independently and then subsequently bind to fibrinogen. Regardless of the actual molecular mechanism, the recombinant A-subunit protein should incorporate into a ternary complex with fibrinogen and B-subunit following incubation. Thus, the addition of A-subunit protein (i.e. Tretten) to A-subunit deficient plasma results in the detection and accurate quantification of its activity in the EC-ELISA, which is designed to be dependent on the formation of the ternary fibrinogen:A2B2 complex. To facilitate the ex vivo formation of fibrinogen:A2B2 complexes, various durations of incubation at 37° C. were studied prior to testing, which informed the predicted physiology of complex formation in vivo.

The method of detecting factor XIII activity is based on two discoveries. First, the circulating factor XIII is tightly bound to fibrinogen, which is present in circulation in much greater amounts than factor XIII. Fibrinogen is a well-known blood clotting protein that is made and secreted into the blood primarily by the liver, is formed from alpha, beta, and gamma chains, and has a molecular weight of about 340 kDa. Second, the antifibrinolytic activity of factor XIII is highly dependent on its transglutaminase activity, which catalyzes the cross-linkage between α2-antiplasmin. Alpha-2 antiplasmin (a.k.a., plasmin inhibitor) is a serine protease inhibitor that inactivates plasmin, which plays an important role in fibrinolysis, and is encoded by the SERPINF2 gene Thus, fibrinogen can be used to capture factor XIII, and α2-AP can be used to measure the amount of factor XIII.

Factor XIII is a protransglutaminase that includes two A-subunits and two B-subunits. The B-subunit protects factor XIII from activation in circulation. Thrombin and calcium activate factor XIII in the final phase of the coagulation cascade. Activated factor XIII catalyzes the formation of ε-N-(γ-glutamyl)-lysyl protein crosslinks. See Lorand L., Ann NY Acad Sci. 936, 291-311 (2001). It is preferable to measure factor XIII activity rather than factor XIII levels because factor XIII is relevant physiologically for the activity it provides. Furthermore, the activity of a set amount of factor XIII protein can vary depending on a number of factors, such as the age and state of the factor XIII protein.

Figure 3:
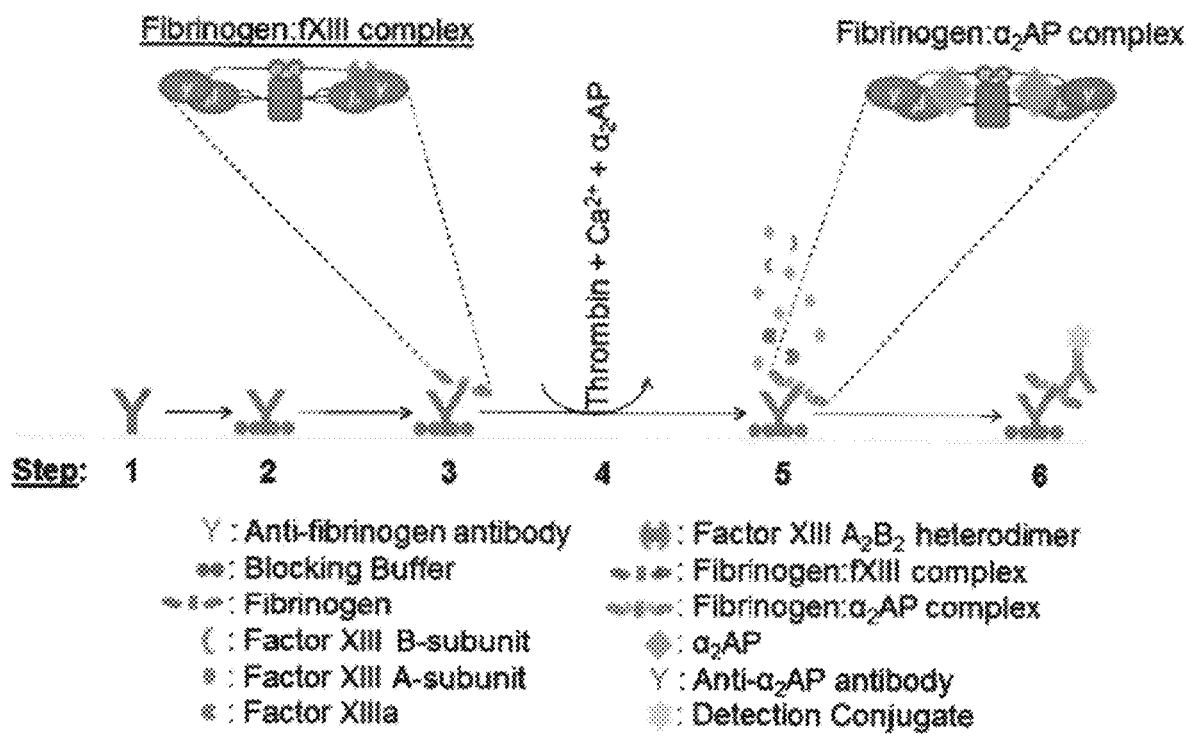
FIG. 3 provides a schematic representation of enzyme capture/enzyme-linked immunosorbent assay (EC-ELISA) for direct measurement of fXIIIa transglutaminase activity. Each step represents a sequential event in a 96-well microtiter plate. Step 1: Coat microtiter well with primary, anti-fibrinogen, enzyme capture antibody. Step 2: Block well against non-specific protein binding. Step 3: Incubate with plasma sample to capture fibrinogen-bound fXIII A2B2. Step 4: After washing, activate fXIII with thrombin and calcium in the presence of excess α2AP (substrate) in the enzymatic step, and wash. Step 5: Detect incorporated α2-AP with secondary, anti-α2-AP antibody conjugated to a detection system (e.g. horseradish peroxidase). Step 6: Conjugate detection using appropriate plate reader settings. (→ Indicates wash steps).
Figure 4:
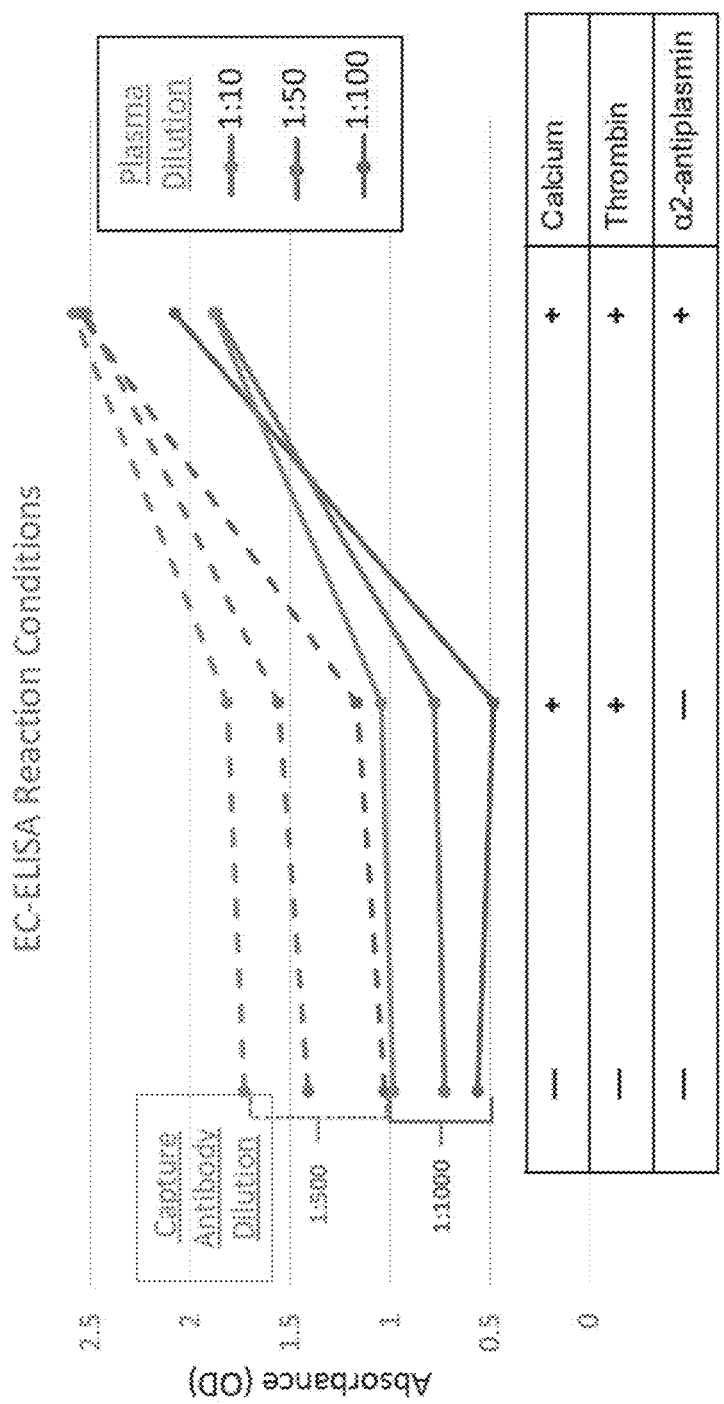
FIG. 4 provides a graph showing evidence of factor XIII-dependent α2-antiplasmin incorporation in the EC-ELISA assay. Varying concentrations of human plasma (1:10, 1:50, 1:100) were introduced for fibrinogen capture and activated in the presence or absence of α2-antiplasmin (substrate). Incorporated substrate was then detected using horseradish peroxidase (HRP)-labeled anti-α2-antiplasmin antibody. Incorporation of α2-antiplasmin above baseline was only detected in the presence of both factor XIII activating conditions and added substrate.

Standard and 'low concentration' titration curves were using congenitally fXIII deficient human plasma (George King Bio-Medical, Inc.). Factor fXIII activities in aliquots of these known titrations were determined, in triplicate, using (1) the optimized EC-ELISA, (2) a NADH-reduction assay (Berichrom Factor XIII Chromogenic, Siemens Healthineers), (3) a NADPH-reduction assay (Technochrom FXIII Kit, Diapharma), and (4) an isopeptidase activity assay (FXIII-Assay Kit, Zedira). The EC-ELISA was calibrated with the previously derived fXIII immunodepleted calibration standards (FIGS. 3 and 4). The commercial assays were performed according to the manufacturers' instructions. The generated data demonstrated: (a) the ability and sensitivity of the EC-ELISA to detect congenital fXIII deficiency and (b) compared the linearity and LLD between the EC-ELISA and these currently available strategies.

The method of detecting factor XIII activity includes the use of antibodies. The two antibodies used herein are referred to as the capture antibody, and the detection antibody. Capture and detection antibodies include polyclonal and monoclonal antibodies, as well as antibody fragments that contain the relevant antigen binding domain of the antibodies. In some embodiments, the capture antibody is a monoclonal antibody. In further embodiments, the detection antibody is a polyclonal antibody.

The term "antibody" as used herein refers to immunoglobulin molecules or other molecules which comprise at least one antigen-binding domain. The term "antibody" as used herein is intended to include whole antibodies, monoclonal antibodies, polyclonal antibodies, chimeric antibodies, humanized antibodies, primatized antibodies, multispecific antibodies, single chain antibodies, epitope-binding fragments, e.g., Fab, Fab' and F(ab')2, Fd, Fvs, single-chain Fvs (scFv), disulfide-linked Fvs (sdFv), fragments comprising either a VL or VH domain, and totally synthetic and recombinant antibodies. The antibodies can be of any type (e.g., IgG, IgE, IgM, IgD, IgA, and IgY), class (e.g., IgG1, IgG2, IgG3, IgG4, IgA1 and IgA2) or subclass of immunoglobulin molecule.

There are over 550 commercially available monoclonal anti-(human)fibrinogen antibodies validated for use in ELISA, a large subset of which are also validated for western blot use. Antibodies are known that bind to fibrinogen regions which are not relevant to the biochemistry necessary for the EC-ELISA (i.e. γ390-396 and α303). Fibrinogen-specificity was confirmed in western blot experiments with fibrinogen standards. A similar strategy was utilized to define appropriate α2-AP antibodies which do not bind at the N-terminus (near Gln14). Western blots confirmed that α2-AP specificity also indicates which α2-AP isoforms are detectable by the antibodies. There are over 50 commercially available monoclonal anti-(human)α2-AP antibodies validated for use in ELISA systems, a subset of which are validated for western blotting.

Antibodies are designed for specific binding, as a result of the affinity of complementary determining region of the antibody for the epitope of the biological analyte. An antibody "specifically binds" when the antibody preferentially binds a target structure, or subunit thereof, but binds to a substantially lesser degree or does not bind to a biological molecule that is not a target structure. In some embodiments, the antibody specifically binds to the target analyte (e.g., fibrinogen or α2-AP) with a specific affinity of between $10^{-8}$ M and $10^{-11}$ M. In some embodiments, an antibody or antibody fragment binds to the target analyte with a specific affinity of greater than $10^{-7}$ M, $10^{-8}$ M, $10^{-9}$ M, $10^{-10}$ M, or $10^{-11}$ M, between $10^{-8}$ M-$10^{-11}$ M, $10^{-9}$ M-$10^{-10}$ M, and $10^{-10}$ M-$10^{-11}$ M. In a preferred aspect, specific activity is measured using a competitive binding assay as set forth in Ausubel FM, (1994). Current Protocols in Molecular Biology. Chichester: John Wiley and Sons ("Ausubel"), which is incorporated herein by reference.

Proteins including antigens, such as fibrinogen or α2-AP, may be used to generate antibodies. One skilled in the art will recognize that the amount of polypeptide used for immunization will vary based on a number of factors, including the animal which is immunized, the antigenicity of the polypeptide selected, and the site of injection. The polypeptides used as an immunogen may be modified as appropriate or administered in an adjuvant in order to increase the peptide antigenicity. In some embodiments, polypeptides, peptides, haptens, and small compounds may be conjugated to a carrier protein to elicit an immune response or may be administered with an adjuvant. e.g. incomplete Freund's adjuvant.

Protocols for generating antibodies, including preparing immunogens, immunization of animals, and collection of antiserum may be found in Antibodies: A Laboratory Manual, E. Harlow and D. Lane, ed., Cold Spring Harbor Laboratory (Cold Spring Harbor, N.Y., 1988) pp. 55-120 and A. M. Campbell, Monoclonal Antibody Technology: Laboratory Techniques in Biochemistry and Molecular Biology, Elsevier Science Publishers, Amsterdam, The Netherlands (1984). In addition, antibodies for both fibrinogen and α2-AP are commercially available.

Monoclonal antibodies may be produced in animals such as mice and rats by immunization. B cells can be isolated from the immunized animal, for example from the spleen. The isolated B cells can be fused, for example with a myeloma cell line, to produce hybridomas that can be maintained indefinitely in in vitro cultures. These hybridomas can be isolated by dilution (single cell cloning) and grown into colonies. Individual colonies can be screened for the production of antibodies of uniform affinity and specificity. Hybridoma cells may be grown in tissue culture and antibodies may be isolated from the culture medium. Hybridoma cells may also be injected into an animal, such as a mouse, to form tumors in vivo (such as peritoneal tumors) that produce antibodies that can be harvested as intraperitoneal fluid (ascites). The lytic complement activity of serum may be optionally inactivated, for example by heating.

The term "antibody fragment" as used herein is intended to include any appropriate antibody fragment which comprises an antigen-binding domain that displays antigen binding function. Antibodies can be fragmented using conventional techniques. For example, F(ab')2 fragments can be generated by treating the antibody with pepsin. The resulting F(ab')2 fragment can be treated to reduce disulfide bridges to produce Fab1 fragments. Papain digestion can lead to the formation of Fab fragments. Fab, Fab' and F(ab')2, scFv, Fv, dsFv, Fd, dAbs, T and Abs, ds-scFv, dimers, minibodies, diabodies, bispecific antibody fragments and other fragments can also be synthesized by recombinant techniques or can be chemically synthesized. Techniques for producing antibody fragments are well known and described in the art. Antibody fragments, including single-chain antibodies, may comprise the variable region(s) alone or in combination with the entirety or a portion of the following: hinge region, CH1, CH2, and CH3 domains.

The method includes the step of immobilizing or having obtained a capture antibody to a solid support. The capture antibody can be bound to the solid support using a binding reagent, or in other embodiments, it can be non-specifically adsorbed to the surface of the solid support. A variety of binding reagents for adhering capture antibodies to a substrate are known to those skilled in the art. For examples, various chemical reagents (e.g., coupling agents, such as dialdehydes, carbodiimides, dimaleimides, bis-imidates, bis-diazotized benzidine) can be used as binding reagents. Alternately, the method can include use of a solid support bearing an immobilized capture antibody that was previously prepared or obtained.

As used herein, the term "solid support" refers to any material capable of having capture antibodies bound thereto. Such solid supports include, but are not limited to, glass, metal, plastic (e.g., polystyrene), or materials coated with a functional group designed for binding of capture reagents or analytes. In some embodiments, the solid support is a microtiter plate.

As used herein, the term "biological sample" means sample material derived from or contacted by living cells. The term "biological sample" is intended to include tissues, cells and biological fluids isolated from a subject, as well as tissues, cells and fluids present within a subject. Biological samples include, e.g., but are not limited to, whole blood, plasma, serum, semen, cell lysates, saliva, tears, urine, fecal material, sweat, buccal, skin, synovial fluid, cerebrospinal fluid, and hair. Biological samples can also be obtained from biopsies of internal organs. Preferably, the biological sample is blood or plasma.

The method can also include the step of the step of obtaining a biological sample from a subject. Alternately, in some embodiments, the biological samples may have already been obtained. Biological samples can be obtained from subjects for diagnosis prognosis, monitoring, or a combination thereof, or for research, or can be obtained from un-diseased individuals, as controls or for basic research. Biological samples can be obtained by any known means including needle stick, needle biopsy, swab, and the like.

A biological sample may be fresh or stored (e.g. blood or blood fraction stored in a blood bank). Samples can be stored for varying amounts of time, such as being stored for an hour, a day, a week, a month, or more than a month. The biological sample may be a bodily fluid expressly obtained for the assays of this invention or a bodily fluid obtained for another purpose which can be sub-sampled for the assays of this invention.

The method includes the step of incubating the biological sample with the capture antibody. Incubation should be carried out for a time and under conditions which allow the capture antibody to bind to a substantial portion of the fibrinogen that is present in the biological sample. Incubation is typically carried out in a well or chamber that retains the biological solution in contact with the capture antibody. Preferably the incubation is carried out under conditions close to physiological conditions, which improve the stability and activity of the proteins involved. For example, in some embodiments, the step of incubating the biological sample with the capture antibody is carried out at about 37° C.

The method also includes various wash steps that are carried out at the completion of several of the steps of the method. For example, wash steps are carried out after initial incubation of the biological sample with the capture antibody, after activating the fibrinogen, and after contacting the immobilized capture antibody with a detection antibody. The wash steps are carried out using an aqueous solution to remove excess sample, reagents, or antibody so that subsequent steps can be carried out without inference from these materials. Methods and conditions for wash steps in an immunoassay are known to those skilled in the art.

Once the capture antibody has been provided an opportunity to bind fibrinogen present in the biological sample, the immobilized capture antibody is contacted with α-thrombin, calcium, and α2-antiplasmin (α2-AP) in order to activate the fibrinogen and form a fibrinogen:α2-AP complex. It is preferable to use a molar excess of α2-AP to encourage the activation and complex formation. Contacting, as used herein, refers to putting the various agents in proximity and under conditions in which they can interact so that the desired effect can occur. For example, the immobilized capture antibody, which should bear fibrinogen from an earlier step, is contacted with α-thrombin, calcium, and α2-antiplasmin (α2-AP) in order to activate the fibrinogen.

The method then includes a step in which a detection antibody is introduced so that it can bind to the α2-AP, thereby indicating the amount of factor XIII present. The detection antibody includes a detection label. The detection label can use enzymatic, fluorescence, chemical (e.g. chemiluminescence), colorimetric, or similar activity that can be detected and corresponds to the amount of α2-antiplasmin (α2-AP) present on the fibrinogen immobilized by the capture antibody. Examples of suitable enzymes for use as a detection label include alkaline phosphatase and horseradish peroxidase. Accordingly, in some embodiments, the detection label comprises horseradish peroxidase. Alternately, other labels can be used instead of enzyme activity Examples of other types of label include a radioisotope, a fluorophore (e.g., fluorescein isothiocyanate (FITC), phycoerythrin (PE)), chemiluminescence, and element particles (e.g., gold particles).

Methods for detecting the detection label vary depending on the nature of the detection label, and include, for example, detection of fluorescence, luminescence, chemiluminescence, absorbance, reflectance, transmittance, birefringence or refractive index (e.g., surface plasmon resonance, ellipsometry, a resonant mirror method, a gating coupler waveguide method or interferometry). Optical methods include microscopy (both confocal and non-confocal), imaging methods and non-imaging methods. Electrochemical methods include voltammetry and amperometry methods. Radio frequency methods include multipolar resonance spectroscopy. Detection of factor XIII activity can be either quantitative or qualitative. In some embodiments, the method provides a quantitative assessment of the level of factor XIII activity.

The method can be used to detect factor XIII in any suitable biological sample. In some embodiments, the biological sample is obtained from a healthy subject. In other embodiments, the biological sample is obtained from a subject having a disease or disorder. For example, in some embodiments, the subject has been diagnosed as having a bleeding disorder.

Diagnosing a Subject with Factor XIII Deficiency

Another aspect of the invention provides a method of diagnosing a subject with factor XIII deficiency. The method of diagnosis includes obtaining or having obtained a biological sample from the subject and detecting factor XIII activity in the biological sample according to the immunoassay described herein, wherein a decreased level of activity as compared with a reference level indicates that the subject has factor XIII deficiency. As used herein, the term "reference level" is intended to mean a control level of factor XIII activity from a healthy individual, or the median value obtained from a number of healthy subjects. The method of diagnosis make use of any of the embodiments of the immunoassay method described herein. For example, in some embodiments, the biological sample is blood or plasma, while in further embodiments the capture antibody is a monoclonal antibody and the detection antibody is a polyclonal antibody. In some embodiments, the factor XIII deficiency identified in the subject is congenital factor XIII deficiency.

The method can also include the step of providing a report indicating the subject has a factor XIII deficiency. For example, the method of diagnosis can include the use of a processor coupled to the immunoassay and adapted to quantify the data representing the signals from the immunoassay, and adapted to perform the multivariate statistical analysis, compare the output value to the first reference value and the second reference value, and calculate the level of factor XIII deficiency; and an output display coupled to the processor and configured to report the level of factor XIII. Subjects having a factor XIII level of below 1 U/dL are severely factor XIII deficient. Subjects having a factor XIII level from 1-4 U/dL are moderately factor XIII deficient.

In some embodiments, the method of diagnosing factor XIII deficiency in a subject is carried out on a subject who has been characterized as having an increased risk of having factor XIII deficiency. For example, in some embodiments, the subject may have been diagnosed as having a bleeding disorder, or has exhibited symptoms of factor XIII deficiency such as umbilical stump bleeding. In further embodiments, the subject may have a family history of factor XIII deficiency. Bleeding disorders are also referred to as coagulopathy, and may cause uncontrolled internal or external bleeding.

In some embodiments, the method of diagnosis is used to identify and or guide treatment of subjects identified as having factor XIII deficiency. Methods of treatment include methods used to treat a variety of bleeding disorders. In addition, treatment of factor XIII deficiency can include replacement therapy to provide additional factor XIII to the subject. Methods of treating congenital factor XIII deficiency are known. See Fadoo et al., J. of Blood Med., 4, 65-73 (2013). Examples of factor XIII treatment include administering natural factor XIII concentrate such as Corifact® and administering recombinant factor XIII (Tretten®).

Monitoring Factor XIII Replacement Therapy in a Subject

Another aspect of the invention provides a method of monitoring factor XIII levels in a subject undergoing factor XIII replacement therapy, comprising obtaining a biological sample from the subject, detecting factor XIII activity in the biological sample using the immunoassay described herein, comparing the detected factor XIII activity with a factor XIII reference value, and altering the factor XIII replacement therapy to increase the level of factor XIII in the subject if the detected factor XIII activity is lower than the factor XIII reference value. The method of monitoring can make use of any of the embodiments of the immunoassay method described herein. For example, in some embodiments, the biological sample is blood or plasma, while in further embodiments the capture antibody is a monoclonal antibody and the detection antibody is a polyclonal antibody.

Treatment of all subjects diagnosed with factor XIII deficiency should be provided to prevent life-threatening bleeding or intracranial hemorrhage. Treatment includes administration of an effective amount of factor XIII every 4-6 weeks to replace the factor XIII activity that is absent in factor XIII deficient subjects. Preferably, sufficient factor XIII is administered to provide factor XIII levels greater than 5 U/dL.

Kits

Another aspect of the invention provides a kit for detecting factor XIII activity in a biological sample. The kit includes a capture antibody on a solid support, wherein the capture antibody comprises an antibody or antibody fragment that specifically binds to fibrinogen, a detection antibody or antibody fragment that specifically binds to α2-antiplasmin, and a package for holding the capture antibody, the detection antibody, and other reagents necessary for detecting factor XIII in a subject using the immunoassay method described herein.

In accordance with another embodiment, the present invention provides one or more kits for determining the level of factor XIII activity in a subject, diagnosing a subject has having factor XIII deficiency, or monitoring factor XIII replacement therapy in a subject. The kits components of the kits will vary depending on whether they are intended for evaluation, diagnosis, or monitoring. Kits for prognosis, diagnosis, or monitoring comprise a substrate including a capture antibody, wherein the capture antibody comprises a fibrinogen binding antibody, or an effective fragment thereof. In some embodiments, the capture antibody is a monoclonal antibody and the detection antibody is a polyclonal antibody. The kit also includes reagents, buffers, and the like for carrying out an immunoassay (e.g., ELISA), which are known to those of ordinary skill in the art. Examples of reagents include reagents α-thrombin, calcium, and α2-antiplasmin. Kits include capture and detection antibodies, or effective fragments thereof, together with a pharmaceutically acceptable carrier for administration of the antibodies.

Kits according to the present invention are assemblies of reagents for testing antibody binding, or administering antibodies. They are typically in a package which contains all elements, optionally including instructions. Instructions may be in any form, including paper or digital. The instructions describe the procedure for using the kit to detect factor XIII in a biological sample. The instructions may be on the inside or the outside of the package. The instructions may be in the form of an internet address which provides the detailed manipulative or analytic techniques. The package may be divided so that components are not mixed until desired.

Components of the kits of the present invention may be in different physical states. For example, some components may be lyophilized and some in aqueous solution. Some may be frozen. Individual components may be separately packaged within the kit. Other useful tools for performing the methods of the invention or associated testing, therapy, or calibration may also be included in the kits, including buffers, enzymes, chemiluminescence reagents, PMAT reagents, gels, plates, detectable labels, vessels, etc. Kits may also include a sampling device for obtaining a biological sample from a subject, such as a syringe or needle.

An example has been included to more clearly describe a particular embodiment of the invention and its associated cost and operational advantages. However, there are a wide variety of other embodiments within the scope of the present invention, which should not be limited to the particular examples provided herein.

EXAMPLE

Development of a Quantitative Factor XIII Activity Assay

Thrombosis and Haemostasis Scientific and Standardization Committee (ISTH-SSC) recommends that "A quantitative functional FXIII activity assay that detects all forms of FXIII deficiency should be used as a 'first-line' screening test". Kohler et al., Journal of thrombosis and haemostasis: JTH, 9(7):1404-6 (2011). Unfortunately, the currently available, clinically-approved FXIII activity assays are technically challenging to implement due to the complex blanking procedures necessary to obtain measurements in the lower end of the dynamic range. Ajzner E, Muszbek L., Journal of thrombosis and haemostasis:JTH, 2(11):2075-7 (2004) Therefore, the assays are often available only in large reference laboratories hindering their utility for rapid diagnosis and direct monitoring of therapy during critical clinical scenarios (i.e. surgery, trauma, pregnancy, etc.). The inconvenience of reference laboratory testing likely contributes to an over reliance on fibrin clot solubility screening assays (e.g. 5M urea clot lysis) that are known to have limited sensitivity and specificity. Jennings et al., International journal of laboratory hematology, 39(4):350-8 (2017). Because these screening assays only detect severe deficiency, this may contribute to the under-recognition of moderate and mild deficiency. Due to these limitations, the official position of the ISTH-SSC is that these tests are not recommended. Nonetheless, many laboratories around the world continue to rely on these assays for frontline testing, likely due to their simplicity. Thus, there is a critical need to develop new, simplified fXIII activity assays able to reliably and accurately measure activity across the pathophysiologic range, including the lower end of the moderate-to-severe range (<10%) in an easily implemented as a platform. Our EC-ELISA demonstrates the proof-of-principle for such an assay.

The present invention leverages recent discoveries regarding factor XIII molecular biology to construct an improved, sensitive, and simplified procedure to measure factor XIII activity that meets the ISTH-SSC expectation of "A quantitative functional FXIII activity assay that detects all forms of FXIII deficiency". Kohler et al., Journal of thrombosis and haemostasis: JTH, 9(7):1404-6 (2011).

The inventors hypothesized that a hybrid enzyme capture/enzyme-linked immunosorbent assay (EC-ELISA) would enable the direct measurement of activated factor XIII (fXIIIa) transglutaminase activity and will would high sensitivity at the low end of the dynamic range (<10%; <0.01 IU/mL).

The currently available, clinically-approved fXIII activity assays are based upon an indirect measurement of activated fXIII (fXIIIa) enzymatic activity. FXIII is a transglutaminase that drives the formation of an isopeptide bond between an acyl group on the side-chain of a glutamine residue and a free amine group (on a neighboring peptide). During an intermediate step of the reaction, a thioacyl complex is formed between the acyl donor peptide and the active site cysteine of fXIIIa and an ammonia ($NH_3$) molecule is released. Thus, the currently available, clinically-approved assays rely on the measurement of "ammonia-release" (i.e. increasing levels of free $NH_3$ in the reaction solution) via an NAD(P)H-dependent glutamate dehydrogenase reaction (FIG. 1). Unfortunately, the assays are highly sensitive to fXIII-independent NAD(P)H-consuming and ammonia-producing reactions that may take place, physiologically, in the plasma sample (e.g. lactate dehydrogenase NADH consumption, γ-glutamyl transferase-dependent glutamine deamidation). Due to these reactions the assays are prone to overestimate FXIIIa activity by as much as 0.02-0.15 IU/mL. Lawrie et al., Journal of thrombosis and haemostasis: JTH, 8(11):2478-82 (2010). Thus, careful plasma blanking procedures are recommended to 'subtract' these non-specific NAD(P)H reducing activities from the apparent fXIIIa measured activity, with variable success that is not reproducible in all labs. Kerlin et al., Journal of thrombosis and haemostasis: JTH. 12(12):2038-43 (2014) In fact, during the course of my work with Novo Nordisk on the Mentor™ studies, the inventors learned that attempts to enhance the low-range sensitivity of the Berichrom® NADH-reduction assay by these blanking procedures was not reliable.

More recently, a highly-sensitive assay that measures the isopeptidase activity of fXIIIa has been developed for research use only. Oertel el al., Analytical biochemistry, 367(2):152-8 (2007). This fluorometric assay relies on the loss of a fluorescent quencher in a manner dependent upon the fXIIIa isopeptidase activity. The lower limit of detection was 2% (0.02 IU/mL), with a quantitation limit of 5% (0.05 IU/mL). Importantly, the NADH-reduction method overestimated fXIIIa activity in comparison to the isopeptidase method. Thus, while this method offers a promising improvement, the role that the isopeptidase activity plays in hemostasis is not known and thus may be less (patho)physiologically relevant to hemostasis than the transglutaminase activity, which is not captured directly by this method. Rijken et al., Journal of thrombosis and haemostasis: JTH., 14(7):1453-61 (2016). Lastly, a number of amine incorporation assays have been developed to directly measure the transglutaminase activity of fXIIIa. These assays rely on accurate measurement of remaining, unincorporated amines after a step to separate them from the substrate. These assays are highly sensitive, but are not commonly employed in the clinical setting due to their time-consuming nature and poor standardization properties. Thus, they are most likely to be utilized only in research laboratory settings.

The hybrid enzyme capture/enzyme-linked immunosorbent assay (EC-ELISA) enables the direct measurement of activated factor XIII (fXIIIa) transglutaminase activity and has high sensitivity at the low end of the dynamic range (<10%; <0.01 IU/mL).

Figure 2:
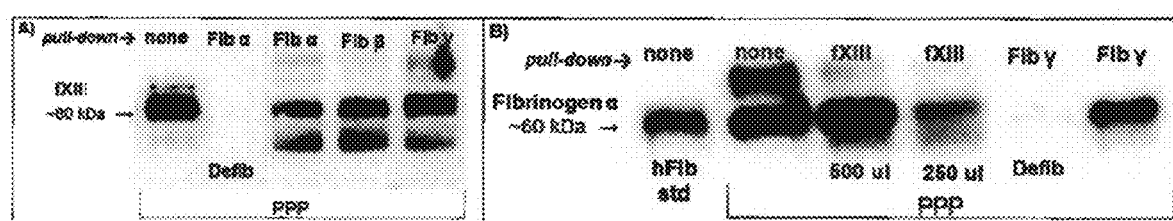
FIG. 2 provides images showing Factor XIII binding interaction with fibrinogen is confirmed by coimmunoprecipitation. Representative immunoblots showing presence of (A) factor XIII or (B) fibrin(ogen) α after co-immunoprecipitation (co-IP) of human plasma. Co-IP was performed on 500 μL aliquots of platelet poor plasma (PPP) subjected to overnight incubation with the indicated antibodies (Fib α: anti-fibrin(ogen) α; Fib β: anti-fibrin(ogen) β; Fib γ: antifibrin(ogen) γ; fXIII: anti-factor XIII-A) and pulled-down with protein A/G agarose beads. Aliquots of PPP were defibrinated with reptilase (0.365 μg/mL) prior to co-IP as additional controls (lanes indicated by "Defib"). (hFib std: human fibrinogen standard).

The invention is based upon two discoveries: (1) That circulating fXIII is tightly bound to fibrinogen (KD~10 nM) via an interaction between the fXIII B-subunit and fibrinogen residues γ390-396 (Byrnes et al., Blood, 128(15):1969-78 (2016)) and (2) The antifibrinolytic activity of fXIII is highly dependent on its transglutaminase activity which catalyzes the cross-linkage between α2-antiplasmin (α2-AP) residue Gln14 and the fibrin α chain residue Lys303 (Kimura S, Aoki N., JBC, 261(33):15591-5 (1986)), directly incorporating a potent plasmin inhibitor (α2-AP) into the fibrin clot. Normal fXIII plasma concentrations are ~0.02-0.03 µM (20-30 nM). Thus, because there is a vast excess of fibrinogen (~9.1 µM) relative to fXIII in the plasma compartment, >98% of circulating fXIII is predicted to be bound to fibrinogen. We have independently confirmed, using co-immunoprecipitation, that fXIII is bound to fibrinogen in human plasma (FIG. 2).

Figure 5B:
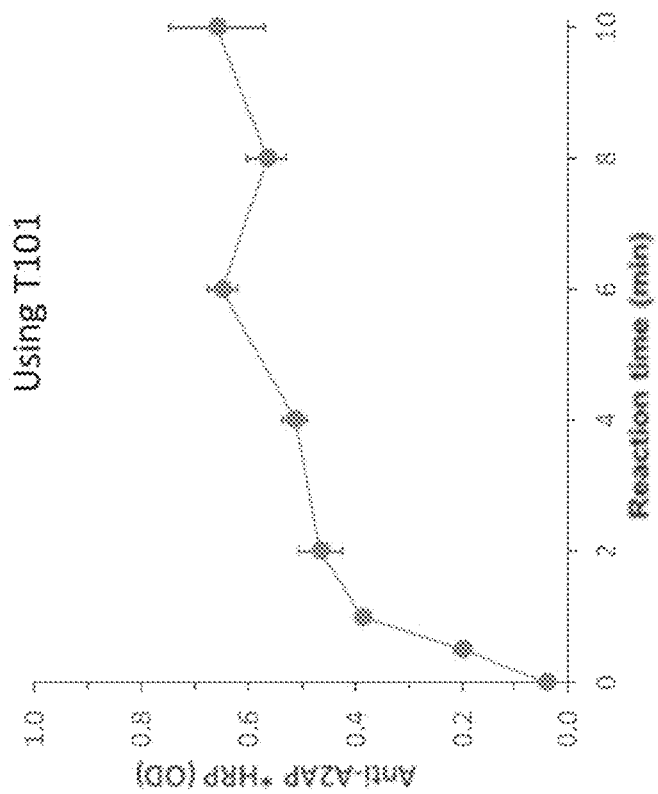
FIGS. 5A and 5B provides graphs showing that factor XIII-dependent α2-antiplasmin incorporation in the EC-ELISA assay is time-dependent. Varying the duration of the EC-ELISA activation step (calcium+thrombin) prior to the addition of two different factor XIII-specific "stop reagents" (iodoacetamide and T101 (chemical name: 1,3,4,5-Tetramethyl-2-[(2-oxopropyl)thio]imidazolium chloride)) demonstrates that α2-antiplasmin incorporation is time-dependent. N=3-4 replicates/time point FIG. 6 provides a graph showing that the EC-ELISA Factor XIII Immunoassay Demonstrates Strong Linearity at the Low End of the Dynamic Range (<10%). Factor XIII activity standard curves were created by the addition of known amounts of recombinant factor XIII A-subunit (Tretten®) into either Factor XIII Congenitally Deficient (Blue) or Factor XIII Immunodepleted (Orange) Plasma. In both cases, there was a strong linear relationship between factor XIII activity and spectrophotometric detection of α2-antiplasmin incorporation (absorbance). N=3-4 replicates per factor XIII concentration
Figure 5A:
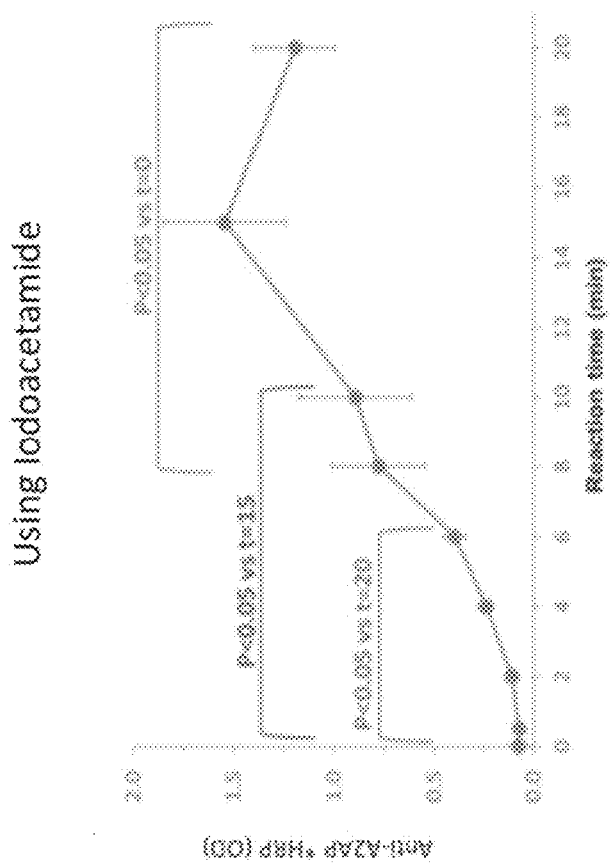

Based on these discoveries, the inventors have designed an assay to capture fXIII with an anti-fibrinogen antibody, activate it in the presence of excess α2-AP, and then detect its activity via an ELISA to detect bound α2-AP with an anti-α2-AP antibody (FIG. 3). The invention includes pre-coating microtiter wells with a primary anti-fibrinogen antibody as an enzyme capture step. Following wash steps; the captured fXIII is activated and cleaves the fibrinopeptides off of the captured fibrinogen via incubation in the presence of α-thrombin and calcium along with excess α2-AP. During this step, activated fXIII (fXIIIa) cross-links α2-AP to the newly formed fibrin monomers, at a rate dependent upon fXIIIa concentration. Introducing iodoacetamide or T101, which are potent fXIIIa inhibitors, as a "stop reagent" to the reaction over longitudinal time points, enables the ability to measure α2-AP incorporation over time (see FIG. 5). Cini et al., Clinical chemistry and laboratory medicine. CCLM/

FESCC., 54(5):805-9 (2016). Following additional wash steps to remove any unbound α2-AP, a secondary anti-α2-AP antibody conjugated to horseradish peroxidase (or another suitable detection conjugate) is utilized to detect cross-linked α2-AP in a conventional ELISA step.

Figure 6:
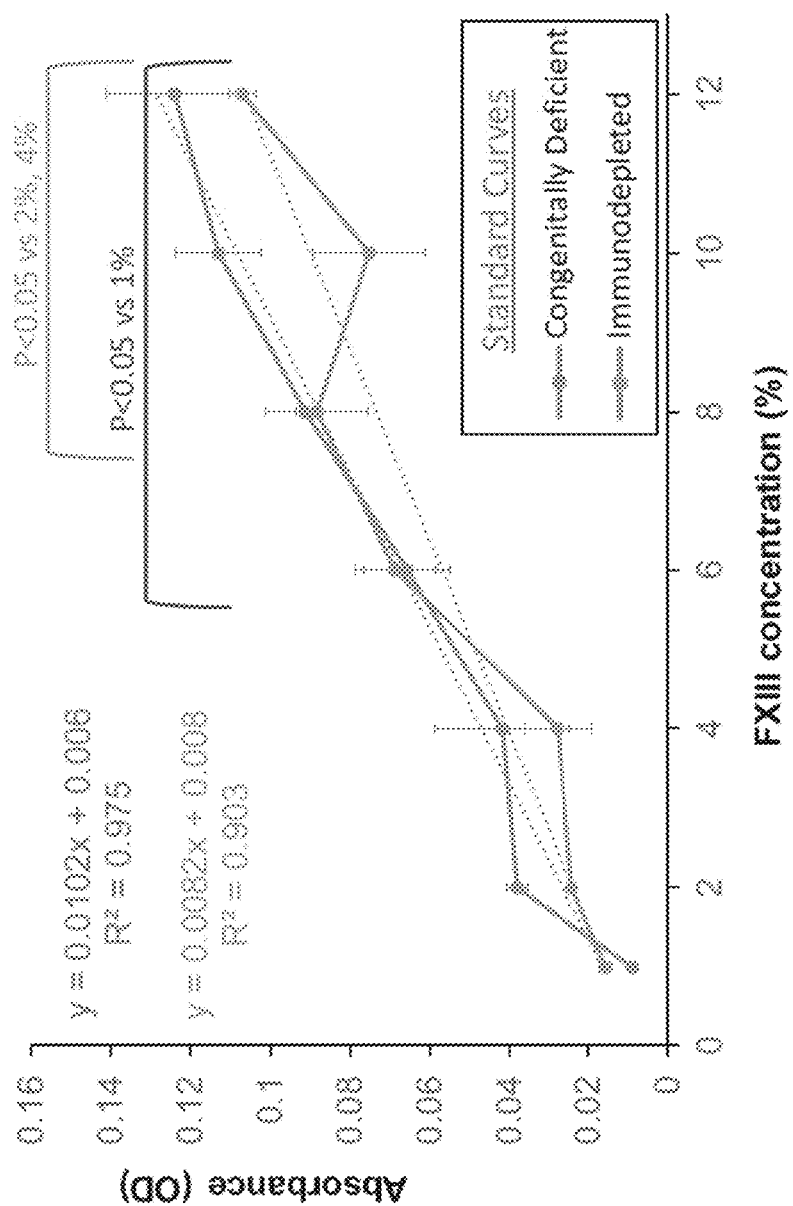

The fXIIIa-dependent crosslinkage of fibrin γ-γ dimers demonstrates first-order Michaelis-Menten enzyme kinetics. Lewis et al., Biochemistry, 36(5):995-1002 (1997). Thus, assuming that fXIIIa-dependent α2-AP-to-fibrin α cross-linking also demonstrates first-order kinetics, it should be possible to estimate fXIIIa activity using only 2, well-spaced stop reagent additions during the linear portion of the reaction. Once optimized, the assay was able to generate a standard curve using known mixtures of pooled normal plasma (PNP) and fXIII-deficient plasma, against which test samples can be measured, as shown in FIG. 6. Importantly to the feasibility of our proposed approach, a similar assay concept has been developed and is currently in clinical use for the detection of type 2N von Willebrand disease, another rare bleeding disorder. Kroner et al., Blood, 87(3):1013-21 (1996).

We have not yet directly assessed the utility of the EC-ELISA for use in fXIII B-subunit congenital deficiency. It is well known that this form of fXIII deficiency is exceedingly rare, with fewer than 20 families having been described in the literature (1). However, based upon the known fXIII biochemistry, it is expected that a sample from a severely B-subunit deficient donor would demonstrate no fXIII activity in the EC-ELISA, since it is designed to be dependent upon formation of the ternary fibrinogen:A2B2 complex, which is dependent upon interactions between the B-subunit and the fibrinogen γ-chain. Further, it is unknown how the assay would perform in plasma from donors with mild or moderate B-subunit deficiency. At this time, the B-subunit molecular region which binds to fibrinogen γ390-396 is not known, but is suspected to reside in sushi domains 1 and/or 10. If the causative mutation in such cases were to leave the fibrinogen binding region of the B-subunit intact, it is possible that the EC-ELISA may be able to detect and quantify residual B-subunit-dependent activity in mild-to-moderate B-subunit deficiency. In contrast, if the mutation were to disrupt the fibrinogen binding region, this assay would not be predicted to detect any residual fXIII activity that may be present in a fibrinogen-independent manner. Because there are no mutational 'hot spots' in the B-subunit gene (F13B), it is possible that such mutations may occur. However, the likelihood of such a mutation is vanishingly rare (i.e. a small subset of an extremely rare condition). In any of these situations, fXIIIa activity, as measured in the proposed EC-ELISA are predicted to be diminished in clinically significant B-subunit deficiency. Thus, the EC-ELISA should meet the ISTH-SSC recommendation for "A quantitative functional FXIII activity assay that detects all forms of FXIII deficiency . . . " Performance of the subsequent steps in the ISTH-SSC algorithm would thus be recommended to determine the subtype of fXIII deficiency. Nonetheless, in future studies, it may be interesting to determine the EC-ELISA profile of either B-subunit deficient donor samples or recombinantly expressed B-subunit designed to mimic known mutations. Souri M, Osaki T, Ichinose A., JBC, 290(19):12027-39 (2015).

The complete disclosure of all patents, patent applications, and publications, and electronically available material cited herein are incorporated by reference. The foregoing detailed description and examples have been given for clarity of understanding only. No unnecessary limitations are to be understood there from. The invention is not limited to the exact details shown and described, for variations obvious to one skilled in the art will be included within the invention defined by the claims.

What is claimed is:

1. A method of detecting factor XIII activity in a biological sample, comprising the steps of: a) immobilizing or having obtained a capture antibody on a solid support, wherein the capture antibody comprises an antibody or antibody fragment that specifically binds to fibrinogen;
  b) incubating the biological sample with the capture antibody;
  c) washing the immobilized capture antibody to remove unbound protein;
  d) contacting the immobilized capture antibody with a-thrombin, calcium, and a2-antiplasmin (AP);
  e) washing the immobilized capture antibody to remove unreacted a2-AP;
  f) contacting the immobilized capture antibody with a detection antibody or antibody fragment that specifically binds to a2-AP, wherein the detection antibody or antibody fragment includes a detection label;
  g) washing the immobilized capture antibody to remove unbound protein; and
  h) determining that factor XIII activity is present if the detection label is detected, wherein the biological sample is whole blood or plasma.

2. The method of claim 1, further comprising the step of obtaining a biological sample from a subject.

3. The method of claim 2, wherein the subject is a human subject.

4. The method of claim 2, wherein the subject has been diagnosed as having a bleeding disorder.

5. The method of claim 1, wherein the capture antibody is a monoclonal antibody.

6. The method of claim 1, wherein the detection antibody is a polyclonal antibody.

7. The method of claim 1, wherein the step of incubating the biological sample with the capture antibody is carried out at about 37° C.

8. The method of claim 1, wherein the detection label comprises horseradish peroxidase.

9. The method of claim 1, wherein the method provides a quantitative assessment of the level of factor XIII activity.

10. The method of claim 1, wherein the solid support is a microtiter plate.

11. A method of diagnosing a subject with factor XIII deficiency, comprising obtaining or having obtained a biological sample from the subject and detecting factor XIII activity in the biological sample according to the method of claim 1, wherein a decreased level of activity as compared with a reference level indicates that the subject has factor XIII deficiency, wherein the biological sample is whole blood or plasma.

12. The method of claim 11, wherein the factor XIII deficiency is congenital factor XIII deficiency.

13. The method of claim 11, wherein the capture antibody is a monoclonal antibody and the detection antibody is a polyclonal antibody.

14. The method of claim 11, wherein the subject is human.

15. A method of monitoring of monitoring factor XIII levels in a subject undergoing factor XIII replacement therapy, comprising obtaining or having obtained a biological sample from the subject, detecting factor XIII activity in the biological sample according to the method of claim 1, comparing the detected factor XIII activity with a factor XIII reference value, and altering the factor XIII replacement therapy to increase the level of factor XIII in the subject if the detected factor XIII activity is lower than the factor XIII reference value, wherein the biological sample is whole blood or plasma.

16. The method of claim 15, wherein the capture antibody is a monoclonal antibody and the detection antibody is a polyclonal antibody.

17. The method of claim 15, wherein the subject is human.

* * * * *